United States Patent [19]
Prammer

[11] Patent Number: 6,051,973
[45] Date of Patent: Apr. 18, 2000

[54] METHOD FOR FORMATION EVALUATION WHILE DRILLING

[75] Inventor: Manfred Prammer, Downingtown, Pa.

[73] Assignee: Numar Corporation, Malvern, Pa.

[21] Appl. No.: 08/996,720

[22] Filed: Dec. 23, 1997

Related U.S. Application Data

[60] Provisional application No. 60/033,986, Dec. 30, 1996.

[51] Int. Cl.[7] .................................................. G01V 3/00
[52] U.S. Cl. .............................................................. 324/303
[58] Field of Search ................................... 324/303, 307, 324/309, 300, 318, 322

[56] References Cited

U.S. PATENT DOCUMENTS

| | | | |
|---|---|---|---|
| 3,508,438 | 4/1970 | Alger et al. | 73/152 |
| 4,710,713 | 12/1987 | Taicher et al. | 324/303 |
| 4,717,876 | 1/1988 | Masi et al. | 324/303 |
| 4,717,877 | 1/1988 | Taicher et al. | 34/303 |
| 4,717,878 | 1/1988 | Taicher et al. | 324/303 |
| 4,728,892 | 3/1988 | Vinegar et al. | 324/309 |
| 4,933,638 | 6/1990 | Kenyon et al. | 324/303 |
| 5,023,551 | 6/1991 | Kleinberg et al. | 324/303 |
| 5,212,447 | 5/1993 | Paltiel | 324/300 |
| 5,280,243 | 1/1994 | Miller | 324/303 |
| 5,289,124 | 2/1994 | Jerosch-Herold et al. | 324/303 |
| 5,309,098 | 5/1994 | Coates et al. | 324/303 |
| 5,349,184 | 9/1994 | Wraight | 250/266 |
| 5,350,925 | 9/1994 | Watson | 250/269.3 |
| 5,363,041 | 11/1994 | Sezginer | 324/303 |
| 5,376,884 | 12/1994 | Sezginer | 324/303 |
| 5,379,216 | 1/1995 | Head | 364/422 |
| 5,381,092 | 1/1995 | Freedman | 324/303 |
| 5,387,865 | 2/1995 | Jerosch-Herold et al. | 324/303 |
| 5,412,320 | 5/1995 | Coates | 324/303 |
| 5,432,446 | 7/1995 | Macinnis et al. | 324/303 |
| 5,486,761 | 1/1996 | Sezginer | 324/303 |
| 5,486,762 | 1/1996 | Freedman et al. | 324/303 |
| 5,497,087 | 3/1996 | Vinegar et al. | 324/303 |
| 5,498,960 | 3/1996 | Vinegar et al. | 324/303 |
| 5,517,115 | 5/1996 | Prammer | 324/303 |
| 5,557,200 | 9/1996 | Coates | 324/303 |
| 5,557,201 | 9/1996 | Kleinberg et al. | 324/303 |
| 5,565,775 | 10/1996 | Stallmach et al. | 324/303 |
| 5,680,043 | 10/1997 | Hurlimann et al. | 324/303 |
| 5,796,252 | 8/1998 | Kleinberg et al. | 324/303 |
| 5,828,214 | 10/1998 | Taicher et al. | 324/303 |

FOREIGN PATENT DOCUMENTS

| | | | |
|---|---|---|---|
| 0 581 666 A3 | 2/1994 | European Pat. Off. | G01V 3/32 |
| 0 649 035 B1 | 4/1995 | European Pat. Off. | G01V 3/32 |

OTHER PUBLICATIONS

International Publication No. WO 98/25164, Publication Date Jun. 11, 1998; from International Application No. PCT/US97/21889, Filed Nov. 26, 1997; Priority Data: Serial No. 08/759,829, Filed Dec. 4, 1996.

Morriss et al., "Hydrocarbon Saturation and Viscosity Estimation from NMR Logging in the Belridge Diatomite," 35th SPWLA Annual Logging Symposium (Jun. 19–22, 1994), pp. 1–24.

Carr et al., "Effects of Diffusion on Free Precision in Nuclear Magnetic Resonance Experiments," *Physical Review*, vol. 94, No. 3 (May 1, 1954), pp. 630–638.

Schlumberger Wireline & Testing, "Combinable Magnetic Resonance tool reliably indicates water–free production and reveals hard–to–find pay zones," (Jun. 1995).

Morriss et al., "Field Test of an Experimental Pulsed Nuclear Magnetism Tool," SPWLA Annual Logging Symposium (Jun. 13–16, 1993), pp. 1–23.

(List continued on next page.)

*Primary Examiner*—Louis Arana
*Attorney, Agent, or Firm*—Pennie & Edmonds LLP

[57] ABSTRACT

A logging while drilling (LWD) and measuring while drilling (MWD) method and device are disclosed for reducing the sensitivity of NMR measurements to tool motions. The invention is based on NMR relaxation measurements determining longitudinal relaxation times T1 instead of the standard T2 measurements, and involves saturating a relatively wide sensitive region of the formation and processing NMR echo signals which originate approximately from the center of the sensitive region.

26 Claims, 5 Drawing Sheets

OTHER PUBLICATIONS

Coates et al., "Core Data and the MRIL Show—A New Approach to 'Formation Factor,'" National SPWLA Convention (Jun. 15, 1992), pp. 1–15.

Kleinberg et al., "Novel NMR Apparatus for Investigating an External Sample," *Journal of Magnetic Resonance,* (1992) pp. 466–485.

Coates et al., "An Investigation of a New Magnetic Resonance Imaging Log," National SPWLA Convention (Jun. 18, 1991), pp. 1–24.

Howard et al., "Proton Magnetic Resonance and Pore–Size Variations in Reservoir Sandstones," *Society of Petroleum Engineers* (1990), pp. 733–741.

Miller et al., "Spin Echo Magnetic Resonance Logging: Porosity and Free Fluid Index Determination," *Society of Petroleum Engineers* (1990), pp. 321–334.

Kenyon et al., "Pore–Size Distribution and NMR in Microporous Cherty Sandstones," SPWLA Thirtieth Annual Logging Symposium (Jun. 11–14, 1989), pp. 1–24.

*Schlumberger Technology News—Oilfield Bulletin,* "Fifth Generation Nuclear Magnetic Resonance Logging Tool: A Major Advance in Producibility Measurement Technology," (Jul. 1995) (2 pp.).

Akkurt et al., "NMR Logging of Natural Gas Reservoirs," SPWLA 35th Annual Logging Symposium (Jun. 26–29, 1995).

Prammer, M.G., "NMR Pore Size Distributions and Permeability at the Well Site,", *Society of Petroleum Engineers* (Sep. 25, 1995) pp. 55–64.

Chandler et al., "Improved Log Quality with a Dual–Frequency Pulsed NMR Tool," *Society of Petroleum Engineers* (1994) pp. 23–35.

Straley et al., "NMR in Partiallly Saturated Rocks: Laboratory Insights on Free Fluid Index and Comparison with Borehole Logs," SPWLA Annual Logging Symposium (Jun. 27, 1991) pp. 40–56.

Jackson et al., "Western Gas Sands Project Los Alamos NMR Well Logging Tool Development," Los Alamos National Laboratory (Oct. 1981–Sep. 1982) pp. 1–28.

Clavier et al., "The Theoretical and Experimental Bases of the 'Dual Water' Model for the Interpretation of Shaly Sands," *Journal of Petroleum Technology* (Apr. 1984), pp. 3–15.

Waxman et al., "Electrical Conductives in Oil–Bearing Shaly Sands," *Society of Petroleum Engineers Journal* (1968) pp. 107–122.

6,051,973

METHOD FOR FORMATION EVALUATION WHILE DRILLING

This application is a continuation of provisional application No. 60/033,986 filed Dec. 30, 1996.

FIELD OF THE INVENTION

This invention is directed to a logging while drilling (LWD) and measuring while drilling (MWD) approach for obtaining nuclear magnetic resonance (NMR) data concerning petrophysical properties of a formation. More specifically, the invention is directed to a method and device for reducing the sensitivity of NMR measurements to tool motions.

BACKGROUND OF THE INVENTION

U.S. Pat. No. 5,280,243 to Miller discloses an NMR apparatus and method of use for geophysical examination of a bore hole as it is being drilled. The patented apparatus is connected to the drill bit and follows it through the bore hole as it is being formed. In operation, the apparatus generates a gradient static magnetic field in a region of the bore hole adjacent the apparatus. This static field extends radially with respect to the longitudinal axis of the apparatus and has a generally uniform amplitude along the azimuth with respect to that axis. Next, a pulsed radio frequency magnetic field is generated to excite nuclei in a substantially cylindrical shell around the tool that defines in the formation a sensitive region extending along the length of the tool and having thickness of about 1 mm. Due to this relatively narrow sensitive region, standard wireline NMR relaxation time measurements are difficult to perform with this tool because lateral vibrations during the measurement time would reduce the accuracy of the measurement.

U.S. Pat. No. 5,557,201 to Kleinberg et al. discloses a pulsed NMR device in which the accuracy of the measurement with respect to lateral tool vibrations is enhanced by providing a larger sensitive region. This is achieved by a special tool architecture shown in FIGS. 2A–B, using two tubular permanent magnets 22 with same poles facing each other, and an antenna 26 positioned in the recess between the two magnets. In operation, this tool architecture provides a sensitive region in the formation which is larger laterally, but is greatly reduced along the borehole axis, because of the presence of a single stationary point in the formation. It is expected therefore that vertical tool motions would affect the accuracy of the tool measurements.

Accordingly, it is perceived that there is a need for improved sensitivity of pulsed NMR measurements using pulsed NMR tools with respect to tool motions.

SUMMARY OF THE INVENTION

The present invention concerns a novel method and device for formation evaluation while drilling a borehole using pulsed NMR tools with magnetic fields that are rotationally symmetric about the longitudinal axis of the borehole.

In a preferred embodiment, the method of the present invention is based on NMR relaxation time measurements determining longitudinal relaxation times T1. In particular, the method comprises the steps of generating at least one radio frequency pulse covering a relatively wide range of frequencies to saturate the nuclear magnetization in a cylindrical volume around the tool; transmitting a readout pulse at a frequency near the center of the range of covered frequencies, the readout pulse following a predetermined wait time; applying at least one refocusing pulse following the readout pulse; receiving at least one NMR echo corresponding to the readout pulse; repeating the above steps for a different wait time to produce a plurality of data points on a T1 relaxation curve; and processing the produced T1 relaxation curve to derive petrophysical properties of the formation.

DETAILED DESCRIPTION

Figure 1A:
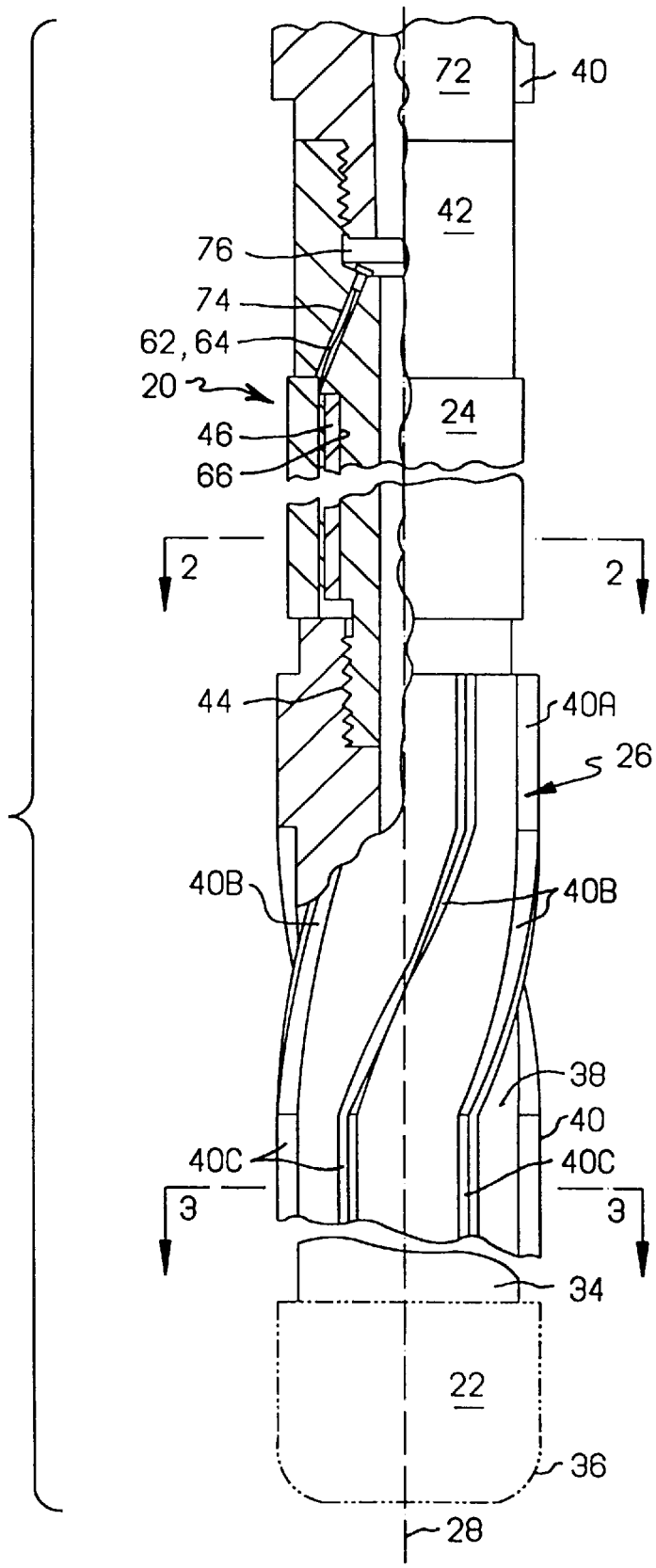
FIG. 1A shows a side elevational view, partly in section, of the lower end of the apparatus disclosed in U.S. Pat. No. 5,280,243.
Figure 1B:
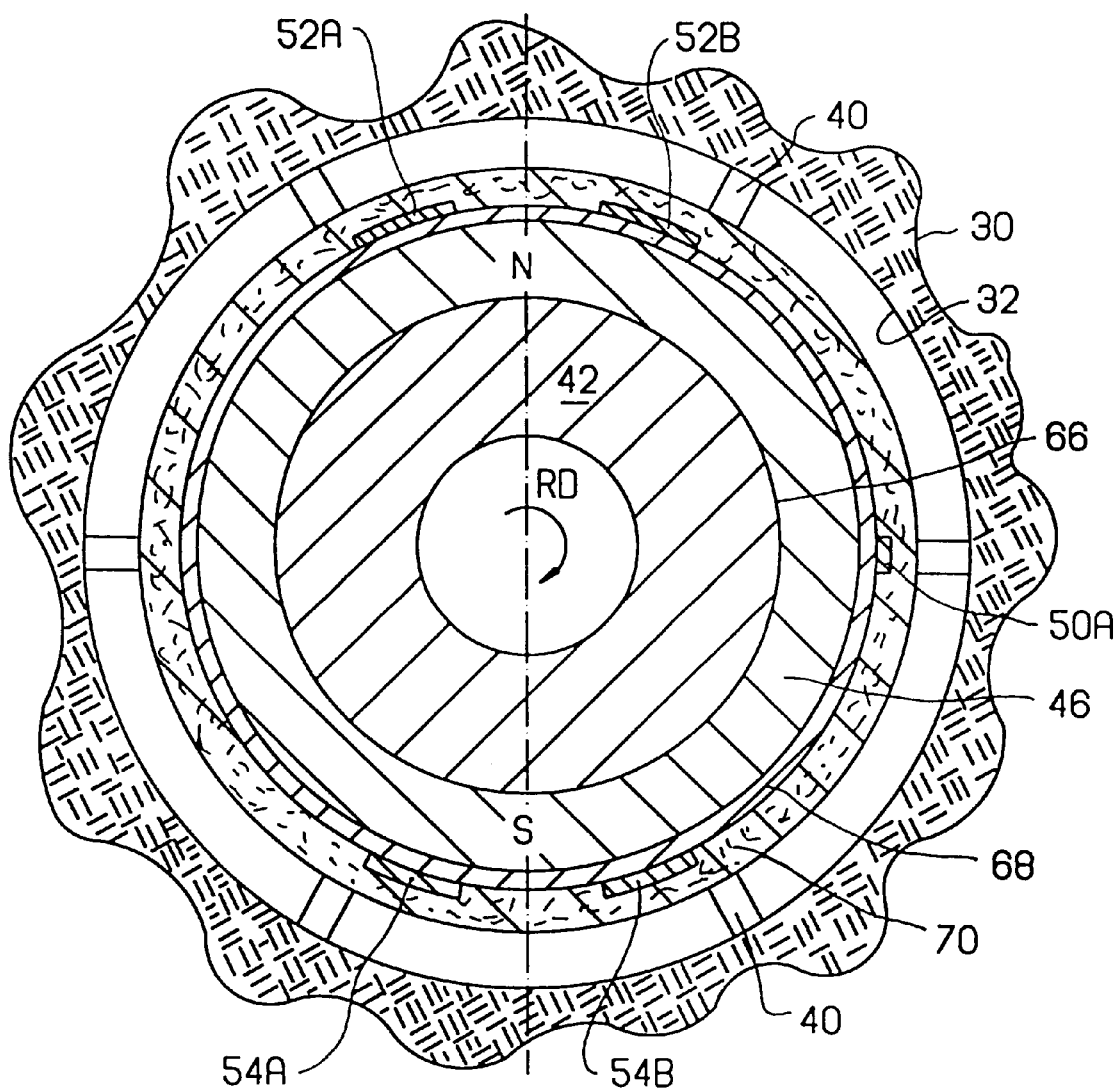
FIG. 1B is an enlarged sectional view taken along the line 2—2 in FIG. 1A.
Figure 2A:
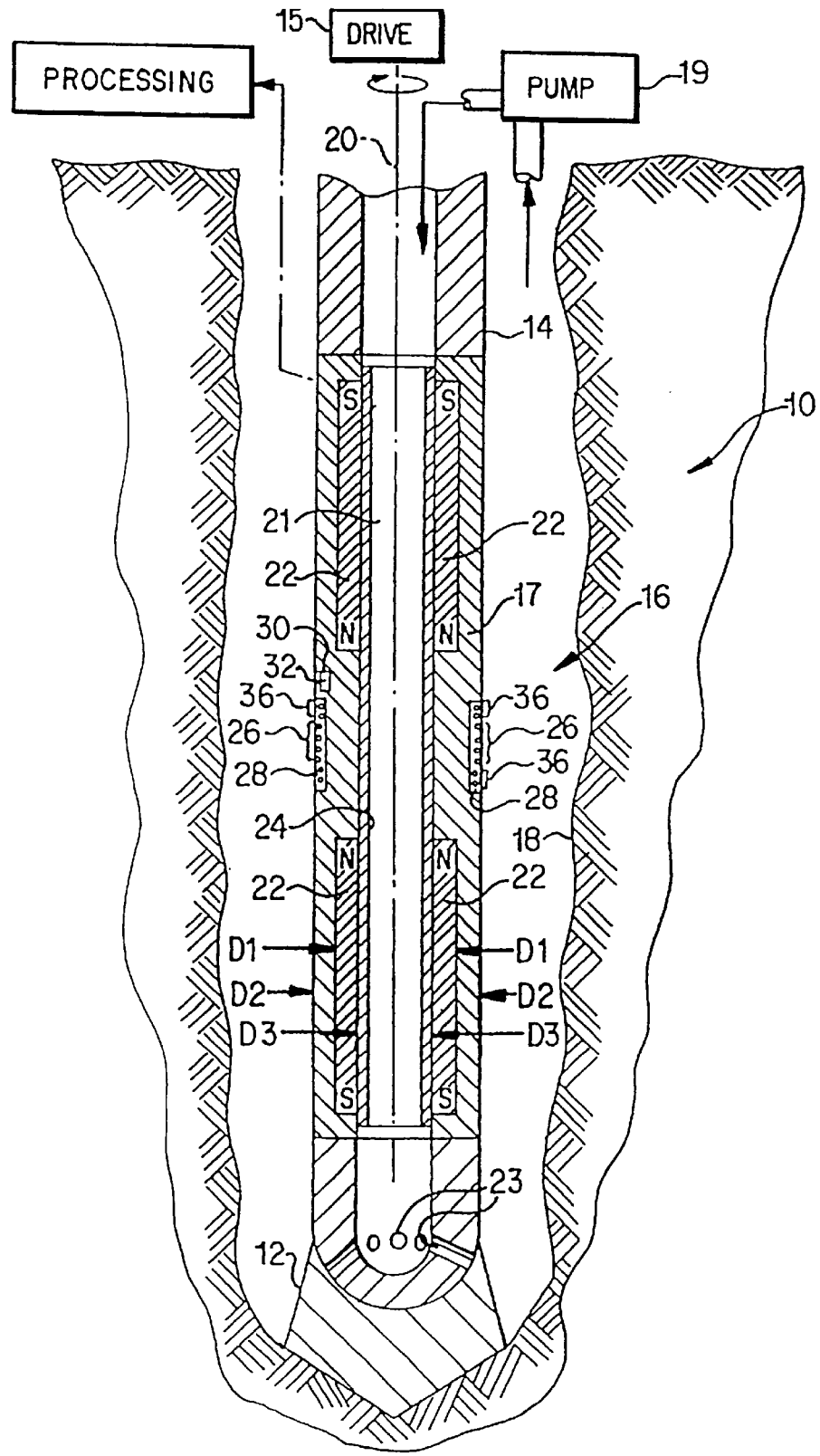
FIG. 2A shows a cross-section of a tool for pulsed NMR formation evaluation disclosed in U.S. Pat. No. 5,557,201.
Figure 2B:
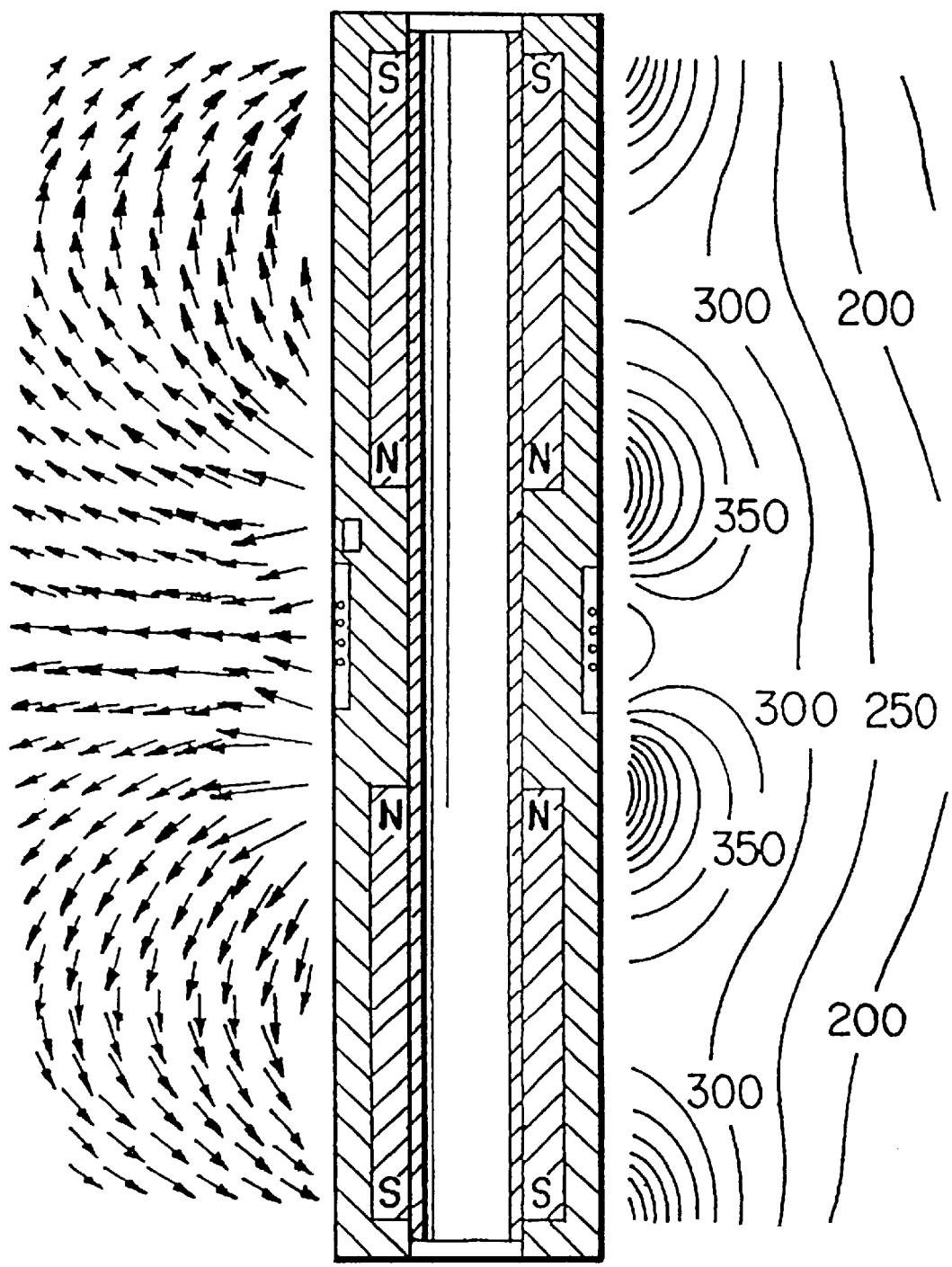
FIG. 2B shows a static field in a vertical plane of the same tool.

The description of the preferred embodiment of the method of the present invention is made with reference to the tool disclosed in U.S. Pat. No. 5,280,243 to Miller, owned by the assignee of the present application. The content of the Miller patent is expressly incorporated herein for all purposes. FIGS. 1A and 1B respectively show a side elevational view, partly in section, of the lower end of the Miller tool and an enlarged sectional view taken along the line 2—2 in FIG. 1A. It should be noted, however, that the method of the present invention can also be used with any tool that generates a rotationally symmetric magnetic field including, for example, the tool disclosed in U.S. Pat. No. 5,557,201 to Kleinberg, illustrated in FIGS. 2A and 2B.

The method of the present invention is based on NMR relaxation time measurements determining longitudinal relaxation times T1, instead of transversal relaxation times T2 that are typically used by a wireline tool. In particular, the method takes advantage of the magnetic field gradient which can be approximated in the proximity of the sensitive volume as a linear fall-off of the magnetic field strength (and also of NMR resonance frequency) in the radial direction.

In a preferred embodiment, at the start of a measurement, one or more radio frequency pulses covering a relatively wide range of frequencies, or using one or more pulses which are frequency swept, are transmitted to saturate the nuclear magnetization in a cylindrical volume around the tool. The range of frequencies can be, for example, 50–100 kHz and is covered in a specific embodiment using a rapid succession of short radio frequency pulses similar to the first pulse in a standard CPMG pulse sequence, or using a single long pulse in a frequency sweep. Changing the range of frequencies used in this step varies the position and the width of the sensitive region in the formation. In a specific embodiment using the Miller tool, a frequency range between 50 and 100 kHz saturates the nuclear magnetization in a cylindrical volume around the tool, where the cylinder has a typical diameter of 14", a height of 24", and thickness of between about ½" to 1".

Following the step of saturation, which typically takes about 1 ms, in accordance with the present invention a readout pulse is transmitted at a frequency near the center of the range of covered frequencies. In alternative embodiments one or more subsequent readout pulses can also be used. In accordance with the present invention, a readout pulse sequence is comprised of a 90° pulse followed by data acquisition, or of a 90° pulse followed by a 180° pulse, followed by data acquisition, where the steps of applying a 180° pulse and data acquisition can be repeated. The readout pulse sequence generally follows a predetermined wait time, as explained in more detail below. In a specific embodiment the readout pulse sequence is transmitted at a center frequency of about 500 kHz, and is followed by one or more refocusing pulses.

Following the readout pulse(s), corresponding NMR echo signals are received, amplified and stored for further processing. Preferably, only the first, the second echo or a combination thereof is retained. In accordance with a preferred embodiment, the amplitude of the retained echo signal is interpreted as the level of nuclear magnetization present after the particular wait time. In the particular example considered above, the center frequency of the NMR echo signals corresponds to about 14" diameter of investigation.

The measurement process described above is repeated for a series of increasing wait times the values of which can, for example, be equally distributed on a logarithmic scale. In a specific embodiment, wait times are stepped through the values 1 ms, 3 ms, 10 ms, 30 ms, 100 ms, 300 ms, 1000 ms and 3000 ms, and the measurement results are stacked to produce several data points on a multi-component T1 relaxation curve. A data point corresponding to the longest wait time is obtained by a readout pulse sequence which is not preceded by a saturation pulse.

Finally, in accordance with the present invention the produced T1 relaxation curve is used to derive petrophysical properties of the formation, as known in the art. In particular, the resultant T1 relaxation curve is processed to extract the dominant T1 relaxation modes, from which amounts of bound water, free water and hydrocarbons are estimated. The characteristic T1 times of the surface-wetting phase can also be used to estimate formation pore size distributions and formation permeability.

It should be noted that since the readout pulse and the signal acquisition have a much smaller bandwidth, typically 5–10 kHz vs. 50–100 kHz saturation bandwidth, the measurement results obtained using the above-described method are less sensitive to lateral motions of the tool, and in particular are not affected by lateral displacements during the wait time period which do not exceed ¼"–½".

Figure 3:
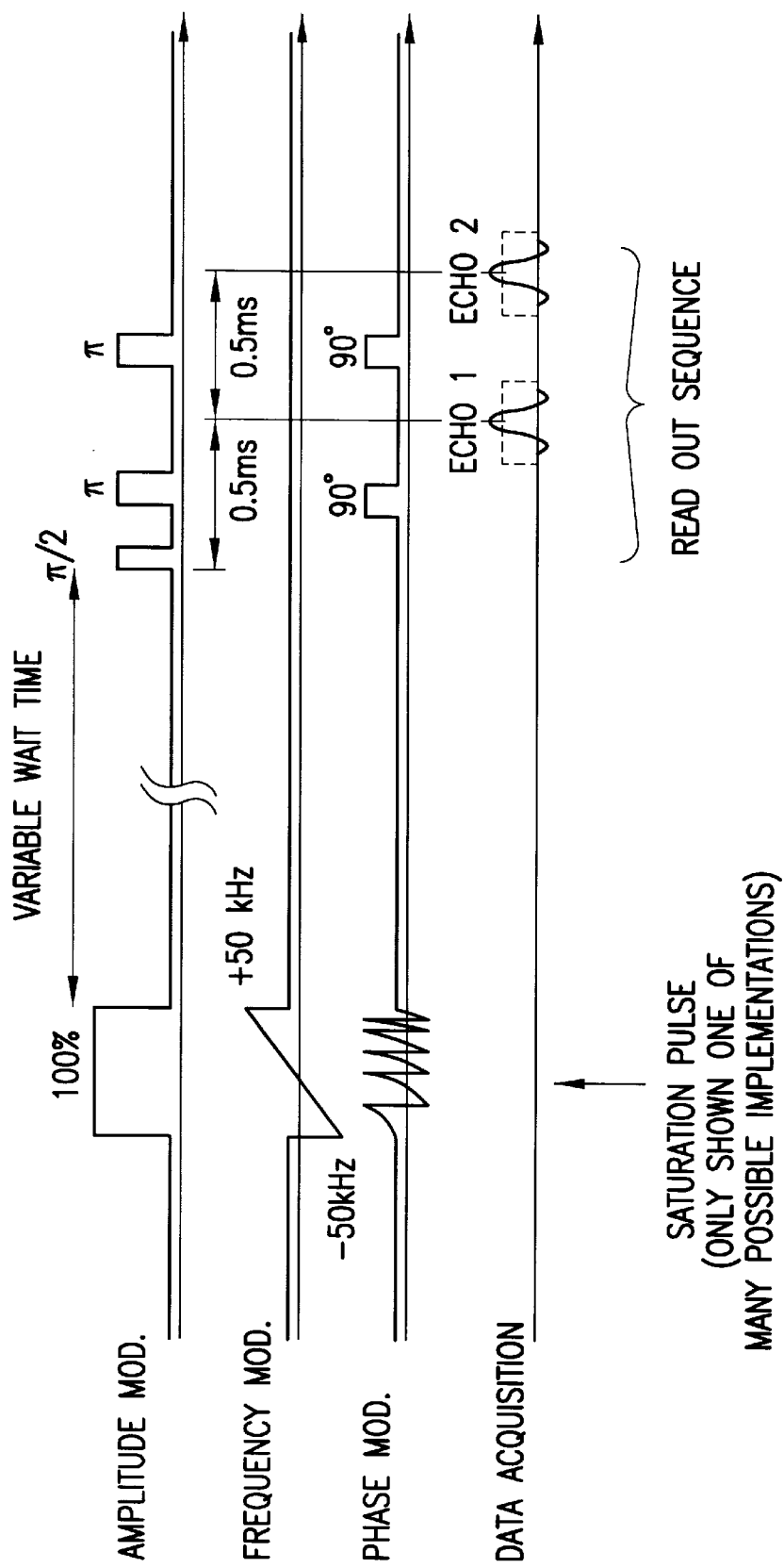
FIG. 3 illustrates a pulse sequence used in a specific embodiment in accordance with the present invention.

An illustration of a pulse sequence used in a specific embodiment of the present invention is shown in FIG. 3.

In accordance with another preferred embodiment of the present invention, the tool used to make the measurements can be fitted with accelerometers, such as those manufactured by Analog Devices, to monitor peak acceleration values along all three axis during the measurement interval. Measurements, during which the peak accelerations indicate that the tool may have been displaced by more than allowable by the extent of the saturation region, are discarded before stacking to further improve the accuracy of the proposed method.

In accordance with another preferred embodiment, the tool is further fitted with hardened steel stand-offs, which, in an in-gauge borehole, allow lateral tool displacements only within the range given by the saturation width. Naturally, the tool may further be provided with accelerometers, as described above, for further accuracy.

While the invention has been described with reference to a preferred embodiment, it will be appreciated by those of ordinary skill in the art that modifications can be made to the structure and form of the invention without departing from its spirit and scope which is defined in the following claims.

I claim:

1. A method for determination of petrophysical properties of a geologic formation using an NMR logging tool, comprising the steps of:
   (a) generating at least one radio frequency pulse covering a relatively wide range of frequencies to saturate nuclear magnetization in a cylindrical volume around the tool;
   (b) transmitting a readout pulse sequence at a frequency near the center of the range of covered frequencies, the readout pulse sequence following a predetermined wait time after the saturation pulse;
   (c) receiving at least one NMR echo corresponding to the readout pulse sequence;
   (d) repeating steps (a), (b) and (c) one or more times for a different wait time to produce a plurality of data points on a T1 relaxation curve; and
   (e) processing the produced T1 relaxation curve to derive petrophysical properties of the formation.

2. The method of claim 1 wherein the produced T1 relaxation curve is processed to derive the amounts of bound water, free water and hydrocarbons in the formation.

3. The method of claim 1 wherein the produced T1 relaxation curve is processed to derive the formation pore size distributions and formation permeability.

4. The method of claim 1 wherein the range of frequencies to saturate the nuclear magnetization is between about 50 kHz and 100 kHz.

5. The method of claim 1 wherein the range of frequencies is covered using a rapid succession of short radio frequency pulses.

6. The method of claim 1 wherein the range of frequencies is covered using a single pulse in a frequency sweep.

7. The method of claim 1 further comprising, prior to the step of receiving said at least one NMR echo, the step of applying at least one refocusing pulse to the readout pulse.

8. The method of claim 1 wherein the step of repeating comprises the steps of transmitting readout pulses following wait times the values of which are equally distributed on a logarithmic scale.

9. The method of claim 1 wherein the step of repeating comprises the steps of transmitting readout pulses following wait times having values of 3 ms, 10 ms, 30 ms, and 100 ms.

10. The method of claim 1 further comprising the step of drilling a borehole in said geologic formation concurrently with steps (a) though (e).

11. The method of claim 1 further comprising the step of monitoring the spatial position of the logging tool during operation, and discarding received NMR echo signals corresponding to tool positions outside a predetermined range.

12. The method of claim 11 wherein the step of monitoring the spatial position is performed using one or more accelerometers mounted on the tool.

13. The method of claim 1 further comprising the step of restricting lateral tool displacements only within a range defined by the saturated volume around the tool.

14. A method for determination of petrophysical properties of a geologic formation during the drilling thereof, comprising the steps of:
   (a) drilling a borehole in a formation;
   (b) saturating nuclear magnetization in a cylindrical volume around the longitudinal axis of the borehole;
   (c) providing at least two readout pulses, each readout pulse at a frequency approximately corresponding to the center of the cylindrical volume;

(d) receiving NMR echo signals corresponding to said at least two readout pulses;

(e) producing a plurality of data points on a T1 relaxation curve from said received NMR echo signals; and (f) processing the produced T1 relaxation curve to derive petrophysical properties of the formation.

15. The method of claim 14 wherein the step of saturating nuclear magnetization in a cylindrical volume comprises the step of generating at least one radio frequency pulse covering a relatively wide range of frequencies.

16. A device for determination of petrophysical properties of a geologic formation using an NMR logging tool comprising:

a drilling means;

a first means for generating at least one radio frequency pulse covering a relatively wide range of frequencies to saturate nuclear magnetization in a cylindrical volume around the tool;

a second means for generating relatively narrow bandwidth readout pulses;

a timing means for providing a predetermined wait time between pulses generated by said first and said second means;

a means for receiving NMR echo signals corresponding to generated readout pulses;

means for processing the received NMR echo signals to produce a T1 relaxation curve to derive petrophysical properties of the formation.

17. The device of claim 16 further comprising accelerometer means for monitoring peak acceleration values along three orthogonal axis of the tool; wherein said means for processing the received NMR echo signals comprises means for discarding echo signals obtained during measurement intervals when peak acceleration values exceed certain threshold.

18. The device of claim 16 further comprising hardened stand-offs, to limit lateral tool displacements within a predetermined range.

19. A method for determination of petrophysical properties of a geologic formation using an NMR logging tool, comprising the steps of:

providing at least one radio frequency (RF) pulse covering a relatively wide range of frequencies to saturate nuclear magnetization in a volume within the geologic formation;

transmitting a readout pulse sequence at a frequency within the range of covered frequencies, the readout pulse sequence following a predetermined wait time after the saturation pulse;

receiving at least one NMR echo corresponding to the readout pulse sequence; and processing said at least one NMR echo to derive petrophysical properties of the formation.

20. The method of claim 19 wherein the range of frequencies to saturate the nuclear magnetization is between about 50 kHz and 100 kHz.

21. The method of claim 19 wherein the range of frequencies is covered using a rapid succession of short radio frequency pulses.

22. The method of claim 19 wherein the range of frequencies is covered using a single pulse in a frequency sweep.

23. The method of claim 19 wherein said readout pulse sequence is a CPMG pulse sequence.

24. A device for determination of petrophysical properties of a geologic formation using an NMR logging tool comprising:

a first means for generating at least one radio frequency pulse covering a relatively wide range of frequencies to saturate nuclear magnetization in a volume within the geologic formation;

a second means for generating relatively narrow bandwidth readout pulses;

a timing means for providing a predetermined wait time between pulses generated by said first and said second means;

a means for receiving NMR echo signals corresponding to generated readout pulses;

means for processing the received NMR echo signals to derive petrophysical properties of the formation.

25. The device of claim 24 further comprising accelerometer means for monitoring peak acceleration values along three orthogonal axis of the tool; wherein said means for processing the received NMR echo signals comprises means for discarding echo signals obtained during measurement intervals when peak acceleration values exceed certain threshold.

26. The device of claim 24 further comprising hardened stand-offs, to limit lateral tool displacements within a predetermined range.

* * * * *